(12) United States Patent
Rezvani

(10) Patent No.: US 7,772,854 B2
(45) Date of Patent: Aug. 10, 2010

(54) HIGH-CONDUCTIVITY CONTACTING-TYPE CONDUCTIVITY MEASUREMENT

(75) Inventor: Behzad Rezvani, Anaheim, CA (US)

(73) Assignee: Rosemount Analytical Inc., Irvine, CA (US)

( * ) Notice: Subject to any disclaimer, the term of this patent is extended or adjusted under 35 U.S.C. 154(b) by 222 days.

(21) Appl. No.: 11/899,959

(22) Filed: Sep. 7, 2007

(65) Prior Publication Data

US 2008/0061804 A1 Mar. 13, 2008

Related U.S. Application Data

(60) Provisional application No. 60/843,300, filed on Sep. 8, 2006.

(51) Int. Cl.
*G01R 27/08* (2006.01)
*G01R 27/02* (2006.01)

(52) U.S. Cl. .................. 324/691; 324/722; 324/444; 324/446

(58) Field of Classification Search ............ 324/691, 324/722, 439, 442, 444, 446
See application file for complete search history.

(56) References Cited

U.S. PATENT DOCUMENTS

| 5,504,430 | A | 4/1996 | Anderson | 324/439 |
|---|---|---|---|---|
| 5,708,363 | A | 1/1998 | Yates et al. | 324/442 |
| 6,278,281 | B1 * | 8/2001 | Bauer et al. | 324/441 |
| 6,369,579 | B1 * | 4/2002 | Riegel | 324/439 |
| 6,377,052 | B1 * | 4/2002 | McGinnis et al. | 324/446 |
| 6,782,736 | B1 * | 8/2004 | Hammer | 73/61.44 |
| 2004/0251919 | A1 * | 12/2004 | Stahlmann et al. | 324/663 |
| 2007/0024287 | A1 * | 2/2007 | Graves et al. | 324/453 |

FOREIGN PATENT DOCUMENTS

| DE | 42 33 110 | 10/1992 |
|---|---|---|
| DE | 198 15 922 | 4/1998 |
| EP | 0 911 639 | 10/1997 |

OTHER PUBLICATIONS

An International Search Report and Written Opinion from foreign application No. PCT/US2007/019589 filed Sep. 7, 2007.
"Dual-Input Intelligent Analyzer, Model 1056," Product Data Sheet PDS 71/1056/rev.B, Emerson Process Management, Feb. 2007.
"Theory and Application of Conductivity," Application Data Sheet ADS 43-018/rev.B, Emerson Process Management, Aug. 2004.

* cited by examiner

*Primary Examiner*—Timothy J Dole
(74) *Attorney, Agent, or Firm*—Christopher R. Christenson; Westman, Champlin & Kelly, P.A.

(57) ABSTRACT

An improved contacting-type conductivity measurement system and method are provided. A first conductivity measurement is obtained by driving a contacting-type conductivity sensor with an excitation voltage at a first frequency, a second conductivity is obtained by driving the contacting-type conductivity sensor with the excitation voltage at a second frequency. The first and second conductivity measurements are used to provide a more accurate conductivity output.

10 Claims, 6 Drawing Sheets

HIGH-CONDUCTIVITY CONTACTING-TYPE CONDUCTIVITY MEASUREMENT

CROSS-REFERENCE TO RELATED APPLICATION

The present application is based on and claims the benefit of U.S. provisional patent application Ser. No. 60/843,300, filed Sep. 8, 2006, the content of which is hereby incorporated by reference in its entirety.

BACKGROUND

Liquid conductivity measurement systems are used for the measurement of conductivity of water and aqueous or non-aqueous solutions in environmental, medical, industrial, and other applications where an indication of the ionic content of the liquid is required.

Liquid conductivity is measured in a variety of contexts to provide a relatively inexpensive parameter that can be sometimes related to bulk ionic concentration. In situations where a single type of ion is present, the conductivity can actually be related to specific ionic concentration. Even in situations where a number of different ionic compounds are present, the measurement of bulk liquid conductivity can still provide very useful information. Accordingly, there has been widespread adoption and utilization of conductivity measurement by the industry for a variety of different purposes. Given the variety of different applications for such systems, it is expected that some will be employed to provide conductivity measurements for low-conductivity liquids, while others will be employed to provide conductivity measurements for high-conductivity liquids.

Typically, contact-based conductivity measurement systems include a conductivity cell and an associated conductivity meter. FIG. 1 illustrates such a system. A conductivity meter generates an AC voltage that is applied to electrodes of the conductivity cell. The meter then senses the resultant current that flows between the electrodes of the cell. This current is generally a function of the conductivity of the liquid to which the cell is exposed and is used to determine the conductance.

The amount of current that flows between the electrodes depends not only the solution conductivity, but also on the length, surface area, and geometry of the sensor electrodes. The probe constant (also called sensor constant or cell constant) is a measure of the current response of a sensor to a conductive solution, due to the sensor's dimensions and geometry. Its units are $cm^{-1}$ (length divided by area), and the probe constant necessary for a given conductivity range is based on the particular conductivity analyzer's measuring circuitry. Probe constants can vary from 0.01 $cm^{-1}$ to 50 $cm^{-1}$ and, in general, the higher the conductivity, the larger the probe constant necessary.

While contacting conductivity based techniques can measure down to pure water conductivity, their primary drawback has been that the sensor itself is susceptible to coating and corrosion, which can drastically lower the reading. In strongly conductive solutions, there can also be polarization effects, which result in non-linearity in the measurement. Providing a contacting-type conductivity sensor that could better measure high-conductivity solutions would allow such contacting-type sensors to be used in a greater variety of applications.

SUMMARY OF THE INVENTION

An improved contacting-type conductivity measurement system and method are provided. A first conductivity measurement is obtained by driving a contacting-type conductivity sensor with an excitation voltage at a first frequency, a second conductivity is obtained by driving the contacting-type conductivity sensor with the excitation voltage at a second frequency. The first and second conductivity measurements are used to provide a more accurate conductivity output.

DETAILED DESCRIPTION OF ILLUSTRATIVE EMBODIMENTS

Embodiments of the present invention generally arise from a unique perception of one or more problems that have troubled the prior art. Contacting conductivity-type sensor readings are difficult to measure due to the excessive error caused by the electrode's metal or graphite interface with the solution. This metal-solution junction is believed to form a constant phase element which electrically can be modeled as a capacitor-resistor network.

Figure 1:
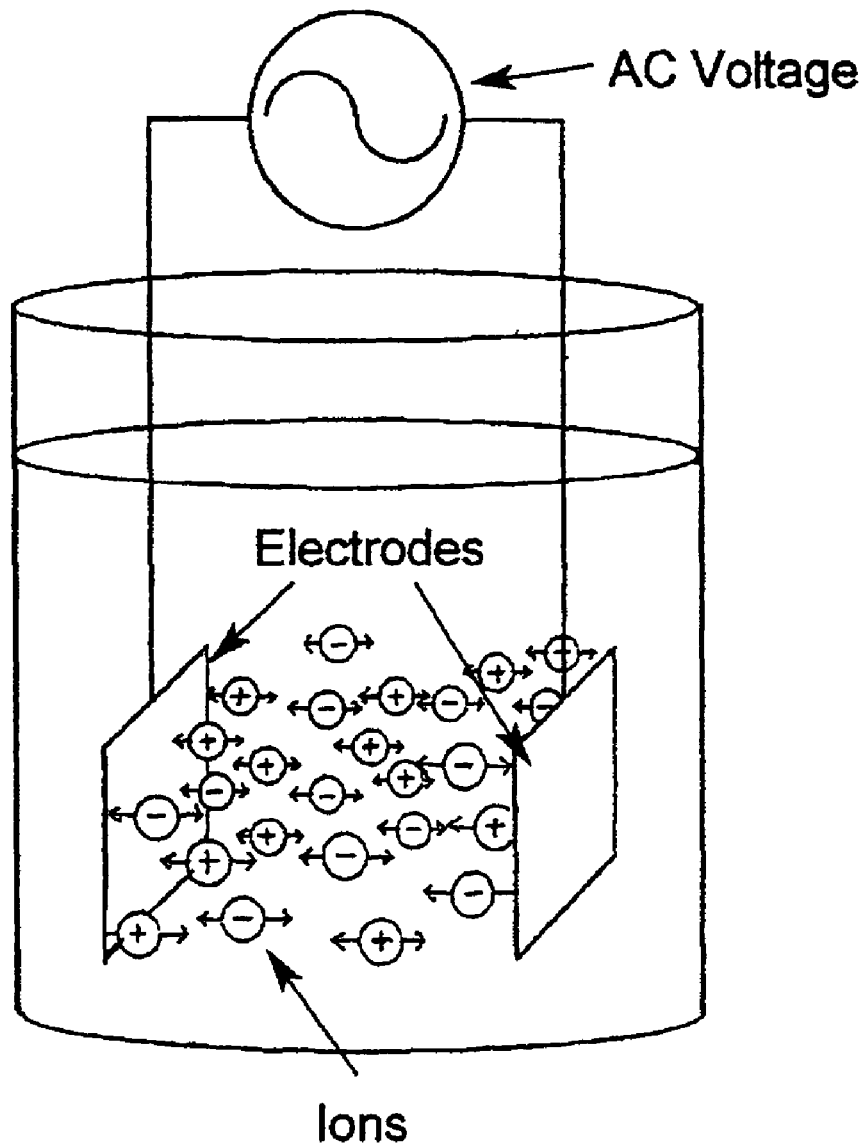
FIG. 1 is a diagrammatic view of a contacting-type conductivity measurement system.
Figure 2:
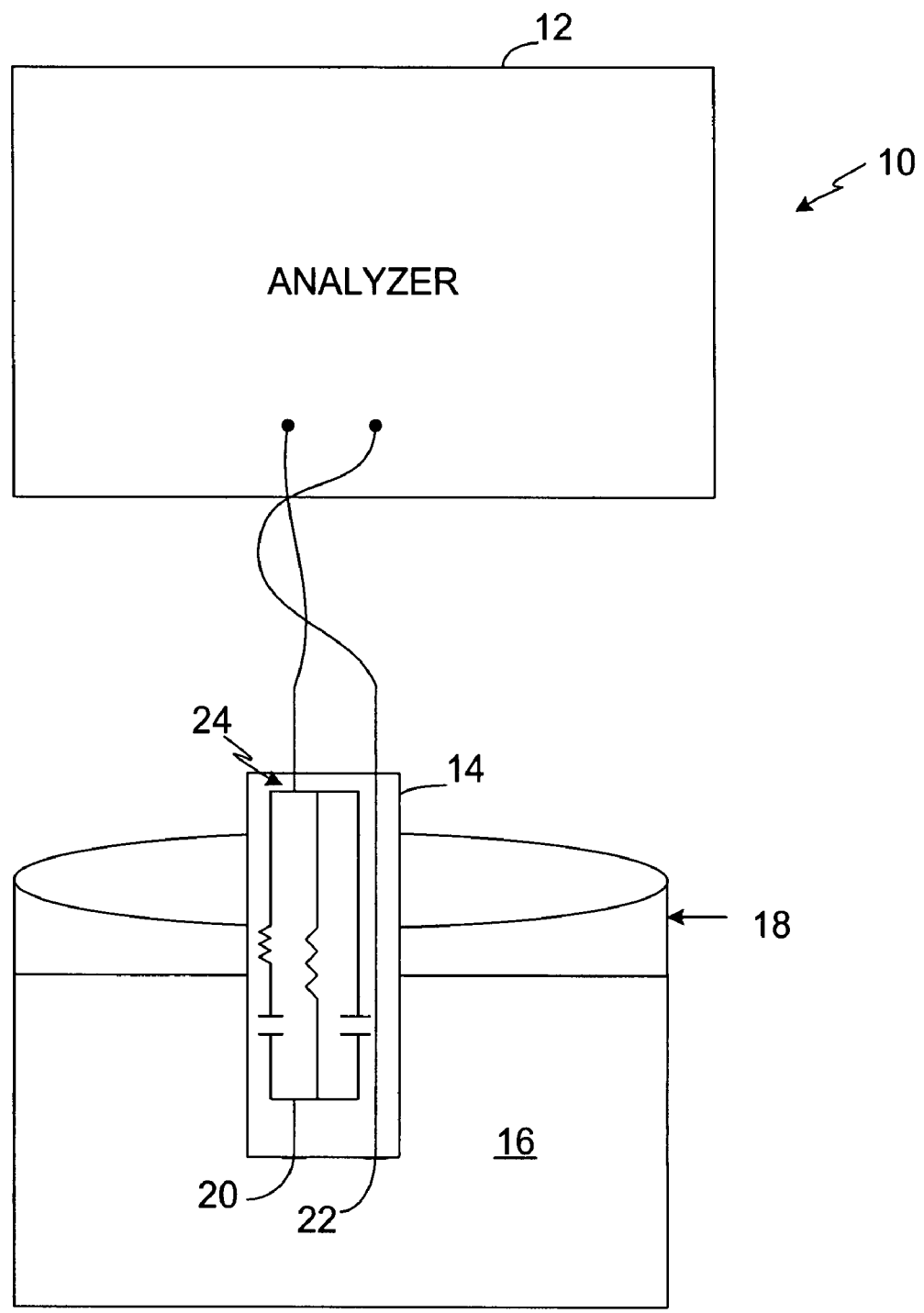
FIG. 2 is a more detailed diagrammatic view of a contacting-type conductivity measurement system.

FIG. 2 is a diagrammatic view illustrating a contacting-conductivity measurement system with which embodiments of the present invention are useful. System 10 includes conductivity analyzer 12 coupled to contacting-type conductivity sensor 14 which is disposed within liquid 16 within container 18. Sensor 14 includes a pair of electrodes 20, 22 that contact liquid 16. As described above, the junction between each of electrodes 20, 22 and liquid 16 forms a constant phase element which has been modeled as a capacitor resistor network 24.

For better accuracy, it is believed that a higher frequency sensor excitation voltage can be applied to measure high conductivities where the metallic electrode junction/solution generates errors that are on the order of, or comparable with, the conductivity of solution 16. While the utilization of a high frequency excitation voltage to drive sensor 14 by analyzer 12 may reduce the error caused by the metal/solution junction, additional errors are introduced due to the cable, sensor and electronics. These errors become greater at higher frequencies, and accordingly, may generate a total error for the system that is, in fact, worse than the lower-frequency excitation.

Embodiments of the present invention generally employ a plurality of individual excitation frequencies to obtain a plurality of conductivity measurements. Conductivity measurements obtained by virtue of the plurality of excitation frequencies are then used, based on some function, to provide a high-conductivity measurement. The resulting measurement is more accurate than either of the low-frequency measurement, or high-frequency measurement, alone.

Analyzer 12 can be any suitable analyzer that is able to effectively drive a contacting-type conductivity sensor. One exemplary analyzer is sold under the trade designation Model 1056. available from the Rosemount Analytical, Inc. division in Irvine, Calif. of Emerson Process Management. Similarly, sensor 14 can be any suitable contacting-type conductivity sensor. Examples of such sensors include those sold as the ENDURANCE™ Series of Conductivity Sensors from Rosemount Analytical Inc. The ENDURANCE™ Series of Conductivity Sensors are available with a cell constant of 0.01, 0.1, and 1.0.

Figure 3:
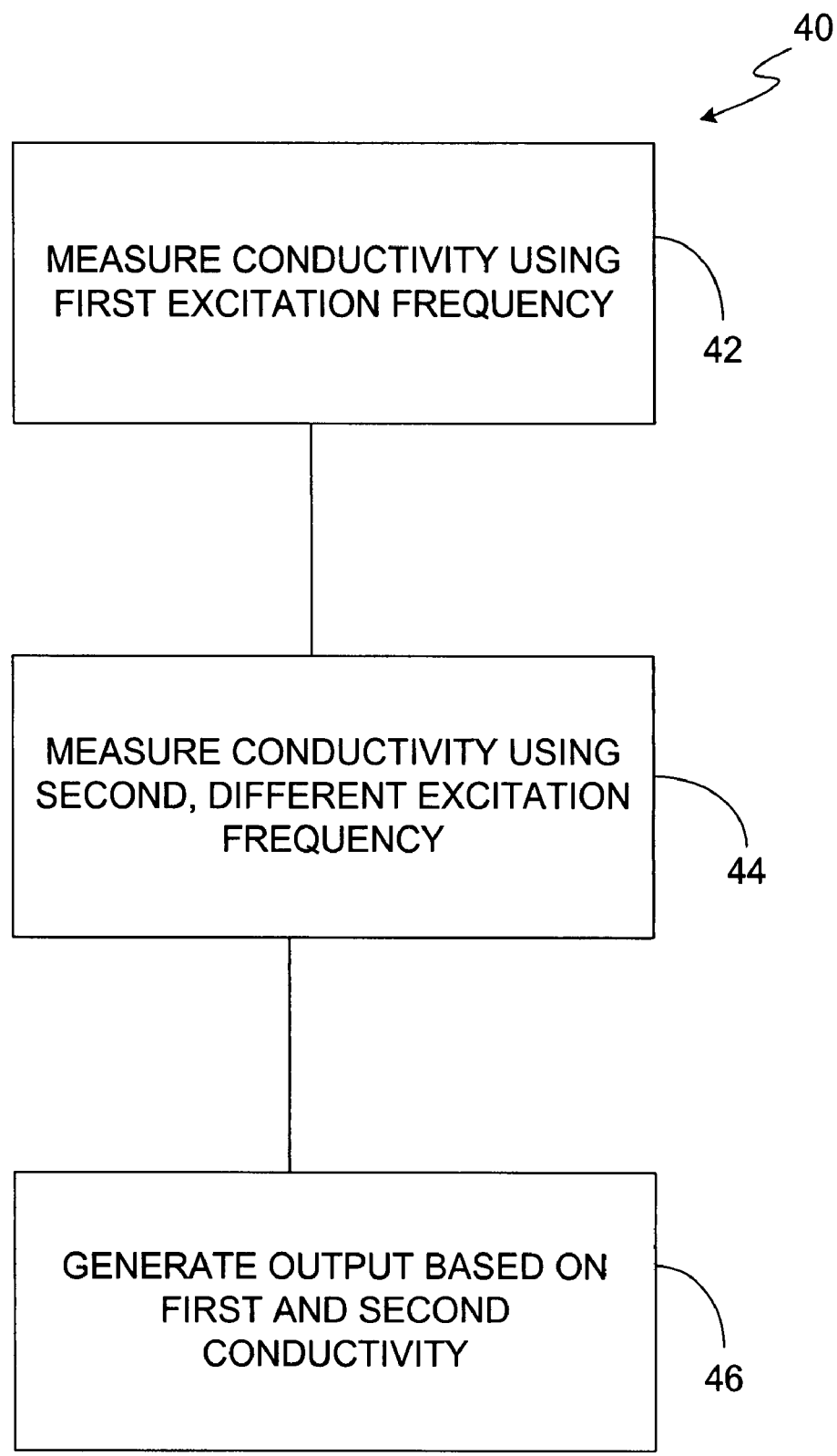
FIG. 3 is a flow diagram of a method of measuring conductivity in accordance with an embodiment of the present invention.

FIG. 3 is a flow diagram of a method 40 of measuring conductivity of a liquid using a contacting-type conductivity sensor in accordance with an embodiment of the present invention. Method 40 begins at block 42 where the conductivity is simply measured using a first excitation frequency. Method step 42 can simply be accomplished by an analyzer, such as analyzer 12 providing an AC voltage to a contacting-type conductivity sensor at an optimum frequency for the best linearity and accuracy of measurement, based upon the application and/or the sensor itself. Accordingly, step 42 is essentially the measurement of conductivity of the solution in accordance with the prior art. However, instead of simply generating an output based on the measured conductivity from step 42, method 40 includes the further step of measuring the conductivity yet again using a second, different, excitation frequency than the first excitation frequency. This is indicated at block 44. The second excitation frequency is preferably higher than the first excitation frequency, and is also preferably determined by analyzer 12. This determination can be based upon the sensor itself, the application, or other suitable factors. Additionally, the frequency at which the second excitation voltage is applied can be selected as a function of the conductance measured in block 42. Accordingly, as the measured conductivity changes in block 42, the manner in which the compensation is generated (by virtue of the selection of the second frequency) can vary. Once block 44 has completed, a second conductivity has been acquired by measuring current flowing through the conductivity sensor in response to the excitation voltage applied at the second frequency. Then, at block 46, the final conductivity is calculated, or otherwise provided, based upon both conductivities acquired during steps 42 and 44. The calculation and/or algorithm for combining the two conductivities can vary. In one embodiment, the final conductivity is simply the average of the two conductivities. In still another embodiment, the calculated conductivity can be a function of the average of the two conductivities and the difference between the two conductivities. However, other more complex calculations can be used wherein the relative weighting of the first and/or second conductivity can be varied based upon such factors the first conductivity measurement itself. Accordingly, as the contacting-type conductivity sensor is exposed to liquids having higher and higher conductivities, the degree to which compensation is provided, by virtue of the selection of the frequency and/or the weighting of the second conductivity can vary accordingly.

While method 40 is described as measuring conductivity using a plurality of excitation frequencies, the measured quantity can also simply be resultant current flow, such that the final conductivity calculation is a function of the first and second measured currents in response to the excitation voltage flowing at the first and second excitation frequencies.

Figure 4:
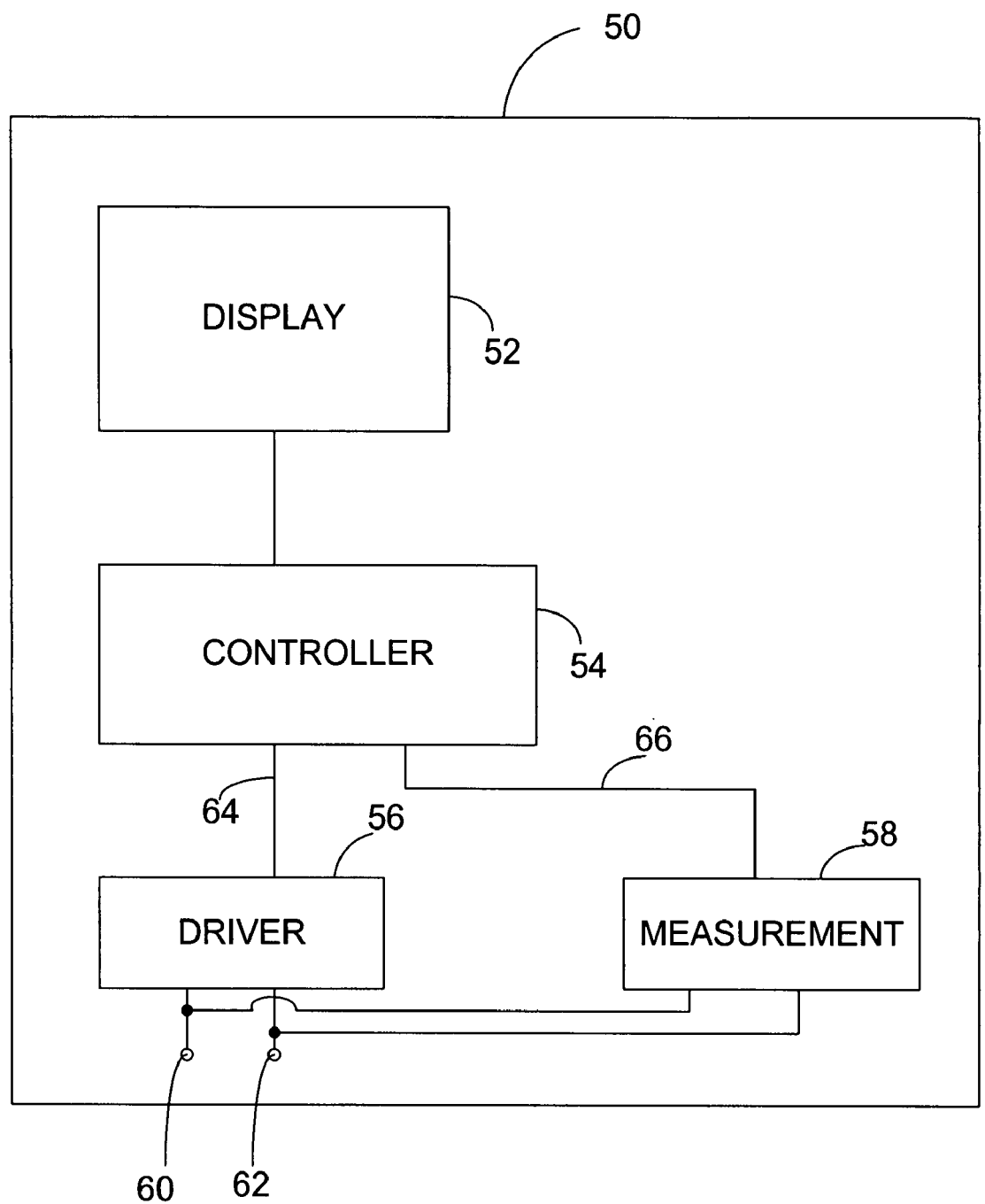
FIG. 4 is a block diagram of a conductivity analyzer in accordance with embodiments of the present invention.

FIG. 4 is a block diagram of a conductivity analyzer 50 in accordance with an embodiment of the present invention. Analyzer 50 includes display 52 coupled to controller 54. Display 52 is preferably a high-contrast liquid crystal display, such as that used in the Model 1056 available from Rosemount Analytical, Inc. Controller 54 includes any suitable device that is able to execute a sequence of instructions to perform a desired function. For example, controller 54 can include any suitable microprocessor and/or microcontroller. Controller 54 is coupled to driver circuitry 56 and measurement circuitry 58. Each of driver circuitry 56 and measurement circuitry 58 are coupled to sensor terminals 60, 62, which, when coupled to a contacting-conductivity sensor, are directly coupled to the contacting electrodes themselves. Driver circuitry 56, in accordance with embodiments of the present invention, is able to generate an excitation voltage across terminals 60, 62 at a plurality of different excitation frequencies. The selection of the excitation frequency is preferably performed via a command, or signal, from controller 54 to driver 56 via signal line 64. Similarly, controller 54 and measurement circuitry 58 are coupled via line 66 such that measurement circuitry 58 communicates data relative to the measured current to controller 54.

To measure a conductivity at the first frequency, controller 54 commands driver 56, via line 64, to generate an alternating voltage across terminal 60, 62 at the first excitation frequency. While that excitation voltage is being generated at the first frequency, measurement circuitry 58 measures the current flowing through the conductivity sensor in response to the excitation voltage. Measurement circuitry 58 preferably includes an analog-to-digital converter that converts the measured current into a digital value that is communicated to controller 54 via line 66. Then, controller 54 commands driver circuitry 56 to select a different, second excitation frequency for the excitation voltage. While the excitation voltage is being generated across terminal 60, 62 at the second frequency, measurement circuitry 58 again measures the current flow through the conductivity sensor. The second value is also preferably converted into a digital parameter and communicated to controller 54. Controller 54 includes suitable arithmetic logic to execute the various calculations and/or algorithms descried above with respect to combining the two conductivity measurements to provide a more accurate output.

Figure 5:
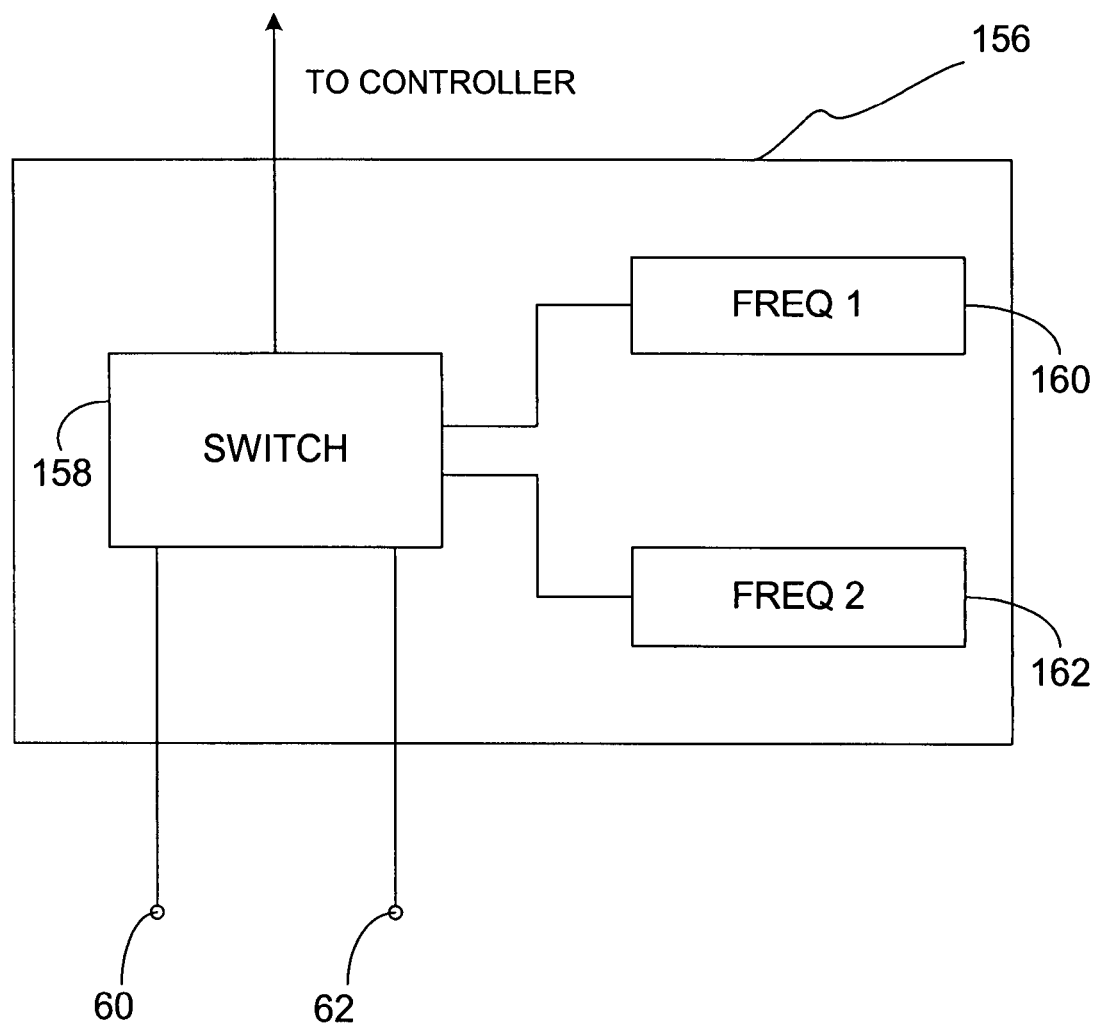
FIG. 5 is a block diagram of driver circuitry of a conductivity analyzer in accordance with an embodiment of the present invention.
Figure 6:
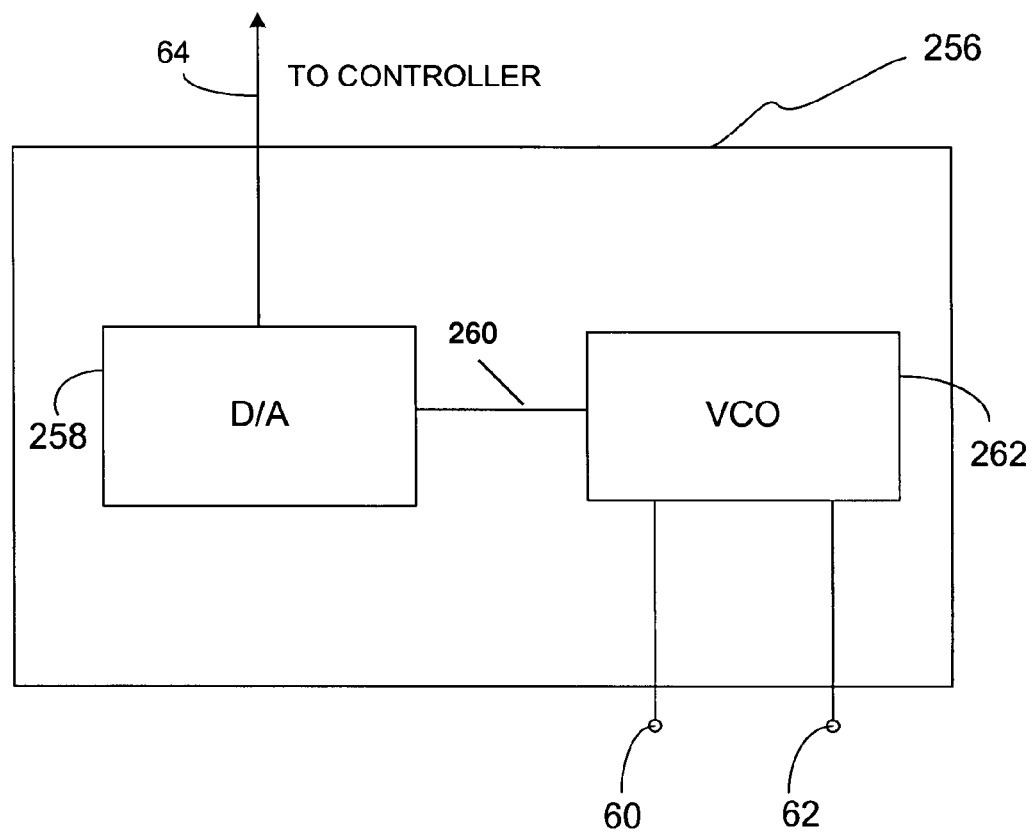
FIG. 6 is a block diagram of driver circuitry of a conductivity analyzer in accordance with an embodiment of the present invention.

The manner in which driver circuitry 56 provides selectable excitation frequencies can vary substantially. FIGS. 5 and 6 provide representative circuits that can be used in accordance with embodiments of the present invention.

FIG. 5 is a block diagram of a suitable driver circuitry that can be used in place of driver circuitry 56 (shown in FIG. 4). Specifically, driver circuitry 156 includes switch 158 that is operably coupled to controller 54 such that controller 54 can, via switch 158, select which of frequency sources 160 and 162 are coupled to terminals 60, 62. Frequency sources 160, 162 can include any suitable oscillation circuits including crystal oscillators, clocks, or other suitable circuits. Additionally, the waveform provided by frequency sources 160, 162 can take any suitable form including square waves, sine waves, sawtooth waves, or any combination thereof.

FIG. 6 is a diagrammatic view of another selectable driver circuitry that can be used in place of driver circuitry 56 (shown in FIG. 4). Specifically, driver circuitry 256 includes a digital-to-analog converter 258 that is operably coupleable to controller 54. D/A converter 258 receives data from controller 54 via line 64 and generates a selectable analog output on line 260. The output on line 260 is provided as an input to voltage controlled oscillator (VCO) 262 which provides the AC voltage having a selectable frequency to terminals 60, 62. Those skilled in the art will appreciate that while the embodiment illustrated with respect to FIG. 5 provides a plurality of selectable frequencies, the embodiment illustrated with respect to FIG. 6 provides a widely varying frequency range based upon the resolution of D/A converter 258. In still another embodiment, the microcontroller itself may set the drive frequency directly, and drive the sensor. The microcontroller can set the frequency based on any suitable computations or algorithms, but preferably sets the frequency based on the conductivity.

The provision of multiple excitation frequencies, while described above as occurring temporally sequentially, can occur in any suitable fashion as long as the resultant current flow from the two excitation voltages can be disambiguated. Specifically, if the two frequencies are sufficiently far apart, suitable filtering circuitry can be used to measure current flow relative to the first frequency, as well as current flow relative to the second frequency. Additionally, the relative timing of the application of the first and second voltage excitation frequencies need not be on a one-two-one basis as described above. Accordingly, the application of the second excitation frequency can be provided at some multiple of the application of the first excitation frequency voltage. Further still, the utilization of compensation based upon the application of the second excitation frequency can be selectably engaged based upon the first conductivity rating itself. Specifically, if the conductivity reading is sufficiently low, and it is determined that given the low conductivity reading, that errors due to the liquid/electrode junction would be small, then compensation may simply be omitted.

Although the present invention has been described with reference to preferred embodiments, workers skilled in the art will recognize that changes may be made in form and detail without departing from the spirit and scope of the invention.

What is claimed is:

1. A method of measuring conductivity of a liquid, the method comprising:
    applying, at a first frequency, an excitation voltage to a contacting-type conductivity sensor disposed within the liquid;
    measuring a first current flow through the liquid in response to the excitation voltage applied at the first frequency to calculate a first conductivity value;
    applying, at a second frequency, different from the first frequency, an excitation voltage to the contacting-type conductivity sensor;
    measuring a second current flow through the liquid in response to the excitation voltage applied at the second frequency to calculate a second conductivity value;
    calculating a conductivity output based upon the average of the first and second conductivity values and the difference between the first and second conductivity values; and
    providing the calculated output.

2. The method of claim 1, wherein the second frequency is higher than the first frequency.

3. The method of claim 1, wherein the second frequency is lower than the first frequency.

4. The method of claim 1, wherein the excitation voltage is applied during a first interval at the first excitation frequency, and applied during a second interval at the second excitation frequency, and wherein the first and second intervals do not overlap.

5. A conductivity analyzer comprising:
    a display for providing a conductivity output;
    a controller coupled to the display;
    driver circuitry operably coupled to at least one output terminal configured to couple to a contacting-type conductivity sensor, the driver circuitry being adapted to provide an excitation voltage at a plurality of selectable excitation frequencies;
    measurement circuitry operably coupled to the at least one output terminal coupleable to the contacting-type conductivity sensor and coupled to the controller, the measurement circuitry being adapted to provide an indication of current flow through the contacting-type conductivity sensor;
    wherein the controller is programmed to cause the driver circuitry to generate an excitation voltage at a first frequency, and cause the measurement circuitry to measure current flowing through the at least one output terminal while the excitation voltage is provided at the first frequency, and wherein the controller is programmed to cause the driver circuitry to generate the excitation voltage at a second frequency, different than the first frequency, and cause the measurement circuitry to measure current flowing through the at least one output terminal while the excitation voltage is applied at the second frequency, and to calculate and provide an indication of conductivity based upon an average of currents measured through the at least one output terminal while the excitation voltage is applied at both the first and second excitation frequencies; and
    wherein the driver circuitry includes a plurality of frequency sources selectably coupleable to the at least one output terminal.

6. The analyzer of claim 5, wherein the conductivity indication is provided through the display.

7. A method of measuring conductivity of a liquid, the method comprising:
    applying, at a first frequency, an excitation voltage to a contacting-type conductivity sensor disposed within the liquid;
    measuring a first current flow through the liquid in response to the excitation voltage applied at the first frequency to calculate a first conductivity value;
    applying, at a second frequency, different from the first frequency, an excitation voltage to the contacting-type conductivity sensor;
    measuring a second current flow through the liquid in response to the excitation voltage applied at the second frequency to calculate a second conductivity value;
    applying a weight to the second conductivity value;
    calculating a conductivity output based upon the first and weighted conductivity values; and
    providing the calculated output.

8. The method of claim 7, wherein the second frequency is selected based upon the first measured current.

9. A method of measuring conductivity of a liquid, the method comprising:
    applying, at a first frequency, an excitation voltage to a contacting-type conductivity sensor disposed within the liquid;
    measuring a first current flow through the liquid in response to the excitation voltage applied at the first frequency to calculate a first conductivity value;

applying, at a second frequency, different from the first frequency, an excitation voltage to the contacting-type conductivity sensor;

measuring a second current flow through the liquid in response to the excitation voltage applied at the second frequency to calculate a second conductivity value;

calculating a conductivity output based upon the first and second conductivity values;

providing the calculated output; and wherein the excitation voltage is applied at the first and second frequencies, simultaneously.

10. A method of measuring conductivity of a liquid, the method comprising:

applying, at a first frequency, an excitation voltage to a contacting-type conductivity sensor disposed within the liquid;

measuring a first current flow through the liquid in response to the excitation voltage applied at the first frequency to calculate a first conductivity value;

applying, at a second frequency, different from the first frequency, an excitation voltage to the contacting-type conductivity sensor;

measuring a second current flow through the liquid in response to the excitation voltage applied at the second frequency to calculate a second conductivity value;

calculating a conductivity output based upon the average of the first and second conductivity values; and providing the calculated output.

\* \* \* \* \*